(12) United States Patent
Yuan et al.

(10) Patent No.: US 11,396,493 B2
(45) Date of Patent: Jul. 26, 2022

(54) AMORPHOUS PYRROLIDINE DERIVATIVE AS PPAR AGONIST AND PREPARATION METHOD THEREOF

(71) Applicant: GUANGDONG RAYNOVENT BIOTECH CO., LTD., Guangdong (CN)

(72) Inventors: Zhiliang Yuan, Shanghai (CN); Zhigan Jiang, Shanghai (CN); Haiying He, Shanghai (CN); Xiao Zhang, Shanghai (CN); Jiwen Xu, Shanghai (CN); Weixiang Zhou, Shanghai (CN); Jian Li, Shanghai (CN); Shuhui Chen, Shanghai (CN)

(73) Assignee: GUANGDONG RAYNOVENT BIOTECH CO., LTD., Guangdong (CN)

( * ) Notice: Subject to any disclaimer, the term of this patent is extended or adjusted under 35 U.S.C. 154(b) by 0 days.

(21) Appl. No.: 16/759,672

(22) PCT Filed: Dec. 20, 2018

(86) PCT No.: PCT/CN2018/122423
§ 371 (c)(1),
(2) Date: Apr. 27, 2020

(87) PCT Pub. No.: WO2019/120257
PCT Pub. Date: Jun. 27, 2019

(65) Prior Publication Data
US 2020/0339508 A1    Oct. 29, 2020

(30) Foreign Application Priority Data
Dec. 21, 2017 (CN) .......................... 201711394677.8

(51) Int. Cl.
*C07D 207/06* (2006.01)

(52) U.S. Cl.
CPC ........ *C07D 207/06* (2013.01); *C07B 2200/13* (2013.01)

(58) Field of Classification Search
None
See application file for complete search history.

(56) References Cited

U.S. PATENT DOCUMENTS 8,642,660 B2    2/2014   Goldfarb

FOREIGN PATENT DOCUMENTS

| CA | 3030431 | * | 1/2018 | ........... C07D 207/06 |
|----|---------|---|--------|------------------------|
| JP | H06329626 A | | 11/1994 | |
| JP | 2019527730 A | | 10/2019 | |
| RU | 2711991 C1 | | 1/2020 | |
| WO | 2002017912 A1 | | 3/2002 | |
| WO | 2006097175 A1 | | 9/2006 | |
| WO | 2007053819 A2 | | 5/2007 | |
| WO | 2008068423 A2 | | 6/2008 | |
| WO | 2018010656 A1 | | 1/2018 | |
| WO | WO 2018/010656 | * | 1/2018 | ........... C07D 207/06 |

OTHER PUBLICATIONS

Thakral Seema et al: "Recent advances in the characterization of amorphous pharmaceuticals by X-ray diffractometry", Advanced Drug Delivery Reviews, vol. 100, May 1, 2016 (May 1, 2016), pp. 183-193.
Zhang, H. et al., and Synthesis and biological evaluation of novel pyrrolidine acid analogs as potent dual PPAR alpha/gamma agoni, Bioorganic & Medicinal Chemistry Letters, 2015, 25 (6), pp. 1196-1205.

* cited by examiner

*Primary Examiner* — Craig D Ricci
(74) *Attorney, Agent, or Firm* — D'Ambrosio & Menon, PLLC; Usha Menon

(57) ABSTRACT

The present invention relates to an amorphous pyrrolidine derivative as a PPAR agonist and a preparation method thereof.

5 Claims, 3 Drawing Sheets

AMORPHOUS PYRROLIDINE DERIVATIVE AS PPAR AGONIST AND PREPARATION METHOD THEREOF

CROSS-REFERENCE TO RELATED APPLICATIONS

This application is based on and claims the benefit of priority from Chinese Patent Application No. CN201711394677.8, filed on 21 Dec. 2017, the entirety of which is incorporated by reference herein.

TECHNICAL FIELD

The present invention relates to an amorphous pyrrolidine derivative as a PPAR agonist and a preparation method thereof.

BACKGROUND

Nonalcoholic fatty liver disease (NAFLD) is the most common liver disease in developed countries or regions, which means that too much fat is accumulated in the liver in the form of triglyceride (hepatocyte tissue with steatosis>5%). In addition to too much fat, patients suffered from NAFLD are associated with hepatocyte damage and inflammation (steatohepatitis), and the latter is just NASH (Non-alcoholic steatohepatitis). Pure steatosis in NAFLD is not associated with increase of short-term morbidity or mortality, but will significantly increase the risks of hepatic cirrhosis, hepatic failure, and hepatocellular carcinoma (HCC) when the pure steatosis progresses to NASH. Hepatic cirrhosis due to NASH is one of the causes of growing liver transplantation. In NASH patients, both the morbidity and the mortality of liver diseases significantly increase, and are closely related to the increased morbidity and mortality of cardiovascular disease. Diagnosis on asymptomatic middle-aged male patients showed that 46% of patients had non-alcoholic fatty liver disease (NAFLD), and 12.2% had NASH. NAFLD patients are mostly men, elderly, hypertensive and diabetic patients. 60-76% of diabetic patients are suffered from NAFLD, and 22% of them are suffered from NASH. Pediatric patients with NAFLD are also increasing year by year, and 38-53% of obese children are suffered from NAFLD. In China, the incidence of non-alcoholic fatty liver has increased to the first.

Currently, there are no FDA-approved drugs to treat this disease, and polyene phosphatidylcholine, silymarin, ursodeoxycholic acid, glycyrrhizic acid and other liver-protective drugs are commonly used in Chinese clinical practice.

Peroxisome proliferator-activated receptor (PPAR), a member of the superfamily of nuclear hormone receptors, is a ligand-activated transcription factor that regulates gene expression, and has primarily three subtypes: PPAP Alpha is mainly expressed in brown fat tissue, liver, heart and skeletal muscle, and plays a major role in the metabolism of bile acid, lipids and sugars; PPAP Delta does not exhibit an expression specificity, and may have an anti-inflammatory effect; and Gamma has a certain effect on insulin resistance. The receptor is associated with a variety of disease states, including dyslipidemia, hyperlipidemia, hypercholesterolemia, atherosclerosis, atherogenesis, hypertriglyceridemia, heart failure, myocardial infarction, vascular disease, cardiovascular disease, hypertension, obesity, inflammation, arthritis, cancer, Alzheimer's disease, skin disease, respiratory disease, eye disease, IBD (irritable bowel disease), ulcerative colitis and Crohn disease. From the mechanisms of multiple beneficial conditions of PPAR for liver function, PPAR agonists are one of the most effective potential drugs for the treatment of fatty liver.

The following compounds are PPAR agonist compounds which have been reported in literatures.

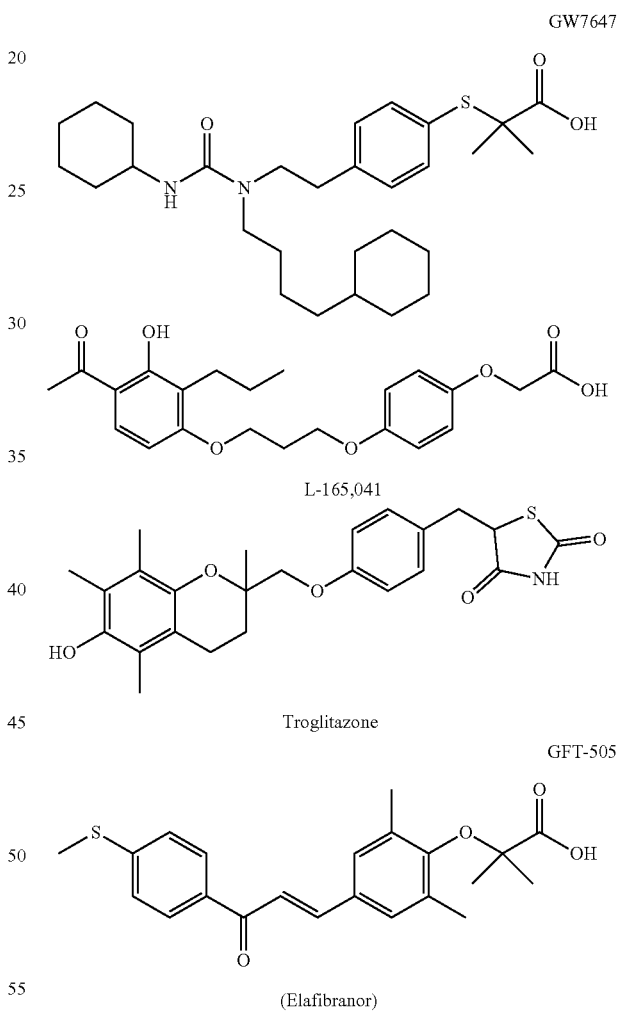

SUMMARY

To solve the shortcomings of the prior art, the first object of the present invention is to provide an amorphous compound represented by formula (I), wherein the amorphous form has considerable stability, and has thus certain medicinal prospects, thereby providing a feasible active pharmaceutical ingredient option for developing the compound represented by formula (I) as a clinical drug.

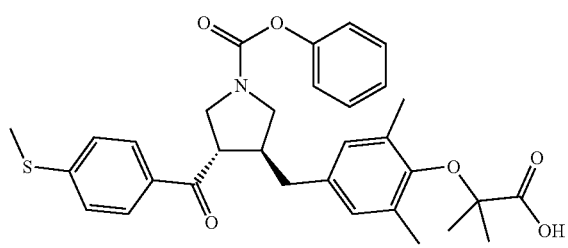

(I)

The aforesaid object of the present invention is performed in accordance with the following technical solutions:

The amorphous form of the compound represented by formula (I) is provided, characterized in that an X-ray powder diffraction (XRPD) pattern of the amorphous form does not have any sharp diffraction peak.

It is well known to those skilled in the art that amorphous form is a thermodynamic high-energy state, which is a thermodynamically metastable structure. The basic particles constituting the compound exhibit a random arrangement in three-dimensional space. X-ray powder diffraction spectrum is one of the most intuitive means for determining an amorphous form. In particular, when a compound exists in an amorphous form, its X-ray powder diffraction pattern usually shows no sharp diffraction peak, that is, the XRPD spectrum appears to have no diffraction peak, or one or several wide and gentle diffraction peaks (often called as "steamed bun peaks" in the art). Those skilled in the art can understand that the wide and gentle diffraction peaks in the XRPD spectrum of amorphous form are relative to the narrow and sharp diffraction peaks in the XRPD spectrum of crystals. In general, the wide and gentle diffraction peaks in the XRPD spectrum of the amorphous form may have 2θ angles with a span of 5° or even more.

In particular, the X-ray powder diffraction pattern of the amorphous form of the compound represented by formula (I) has a wide and gentle diffraction peak at 2θ angle between 10° and 25°.

In an embodiment of the present invention, the amorphous form of the compound represented by formula (I) has an X-ray powder diffraction pattern as shown in FIG. 1.

In some embodiments, the aforesaid amorphous form has a differential scanning calorimetry (DSC) curve with starting points of two endothermic peaks at 69.28±3° C. and 239.33±3° C.

In an embodiment of the present invention, the aforesaid amorphous form has a DSC pattern as shown in FIG. 2.

In some embodiments, the aforesaid amorphous form has a thermogravimetric analysis (TGA) curve with a weight loss reached 0.9958% at 120.00±3° C.

In an embodiment of the present invention, the aforesaid amorphous form has a TGA pattern as shown in FIG. 3.

The second object of the present invention is to provide a method for preparing the amorphous form of the compound represented by formula (I), and the preparation method includes: adding the compound of formula (I) into a solvent for heating with stirring or recrystallization to prepare the amorphous form; wherein the solvent is selected from the group consisting of methanol, ethanol, tetrafuran, ethyl acetate and n-heptane, the stirring temperature of the heating with stirring is 25° C.-45° C., the time of heating with stirring (beating) is 2 h-48 h, and the mass/volume ratio of the compound to the solvent is 1:3.5-6 g/mL in the preparation method.

This method involves stable process, mild reaction conditions, and readily available raw materials, and thus can be used for large-scale industrial production of the amorphous form of the compound of formula (I).

Technical Effect

Surprisingly, the inventor finds that, unlike conventional amorphous compounds which have poor stability and poor medicinal properties, the amorphous form of the compound of formula (I) as described in the present invention has higher stability, which is specially shown in that the amorphous form of the compound of formula (I) has relatively high stability under high temperature, high humidity and other conditions. Based on the existing stability data, it can be judged that the amorphous form of the compound of formula (I) has certain medicinal prospects.

Further, the amorphous form of the compound of formula (I) as described in the present invention exhibits an obvious inhibitory effect on cytokines of PPAR-associated pathways, and it is found that the compound of formula (I) produces a significantly improving effect on liver injury, NAS Score, and liver fibrosis through the CCl4-induced C57BL/6 mouse acute liver injury experiments and MCD diet-induced db/db mouse NASH models.

To sum up, it can be seen that the amorphous form of the compound represented by formula (I) of the present invention has better stability and certain medicinal prospects. Thus, if it proves through detection means that a part or all of the compound represented by formula (I) is present in an amorphous form in APIs and/or preparation products, and it should be considered that the amorphous form of the compound represented by formula (I) as provided in the present invention is utilized. In addition to the X-ray powder diffraction as described above, the detection means can further include differential scanning calorimetry (DSC), infrared spectroscopy (IR), Raman spectroscopy (Raman), solid-state nuclear magnetic resonance (SSNMR), and any other detection means which can prove the use of the amorphous form of the compound represented by formula (I) of the present invention, and any method commonly used by those skilled in the art can be used to remove effects caused by drug excipients or the like, such as a subtractive pattern method.

Definition and Explanation

Unless otherwise stated, the following terms and phrases as used herein are intended to have the following meanings. A particular phrase or term should not be considered uncertain or unclear without specific definition, but should be understood in its ordinary meaning. When a trade name is listed herein, it is intended to refer to its corresponding product or its active ingredients.

The intermediate compounds of the present invention can be prepared by a variety of synthetic methods as well known by those skilled in the art, including the specific embodiments listed below, the embodiments formed by the combination of those embodiments with other chemical synthesis methods, and equivalent alternatives as well known by persons skilled in the art. The preferred embodiments include, but are not limited to, the examples of the present invention.

The chemical reactions of the specific embodiments of the present invention are performed in an appropriate solvent, and the solvent should be suitable for the chemical changes of the present invention as well as the reagents and materials required thereby. To obtain the compounds of the present invention, it is sometimes to be required that persons skilled in the art make modification or selection to the synthesis steps or reaction processes based on the existing embodiments.

Hereinafter the present invention will be described in details by ways of examples. These examples are not intended to limit the present invention in any manner.

All the solvents as used in the present invention are commercially available, which can be used without further purification.

The solvents as used in the present invention are commercially available. The following abbreviations are used in the present invention: DCM represents dichloromethane; DMF represents N,N-dimethylformamide; DMSO represents dimethylsulfone; EtOH represents ethanol; MeOH represents methanol; TFA represents trifluoroacetic acid; TsOH represents p-toluenesulfonic acid; mp represents melting point; EtSO3H represents ethanesulfonic acid; MeSO3H represents methanesulfonic acid; ATP represents triphosadenine; HEPES represents 4-hydroxyethylpiperazine ethanesulfonic acid; EGTA represents ethylene bis(2-aminoethyl ether) tetraacetic acid; $MgCl_2$ represents magnesium dichloride; $MnCl_2$ represents manganese dichloride; and DTT represents dithiothreitol.

1.1 X-Ray Powder Diffraction (XRPD)

Instrument Model: Brook D8 advance (Bruker D8 Advance) X-Ray Diffractometer

Test Method: Appropriately 10-20 mg of sample is used for XRPD detection.

The detailed XRPD parameters are as follows:
Light pipe: Cu, kα, (λ=1.54056 Å)
Light pipe voltage: 40 kV, Light pipe current: 40 mA
Divergence slit: 0.60 mm
Detector silt: 10.50 mm
Anti-scatter silt: 7.10 mm
Scanning range: 4-40 deg
Step: 0.02 deg
Step size: 0.12 second
Rotational speed of sample disk: 15 rpm 1.2 Differential Scanning Calorimetry (DSC)

Instrument Model: TA Q2000 differential scanning calorimeter

Test Method: A sample (~1 mg) was placed in a DSC aluminum pot for testing, and the method includes: heating the sample at a heating rate of 10° C./min from 25° C. to 350° C. under the condition of 50 mL/min $N_2$.

1.3 Thermal Gravimetric Analysis (TGA)

Instrument Model: TA Q5000IR thermal gravimetric analyzer

Test Method: A sample (2-5 mg) was placed in a TGA platinum pot for testing, and the method includes: heating the sample at a heating rate of 10° C./min from room temperature to 350° C. under the condition of 25 mL/min $N_2$.

DETAILED DESCRIPTION

Figure 1:
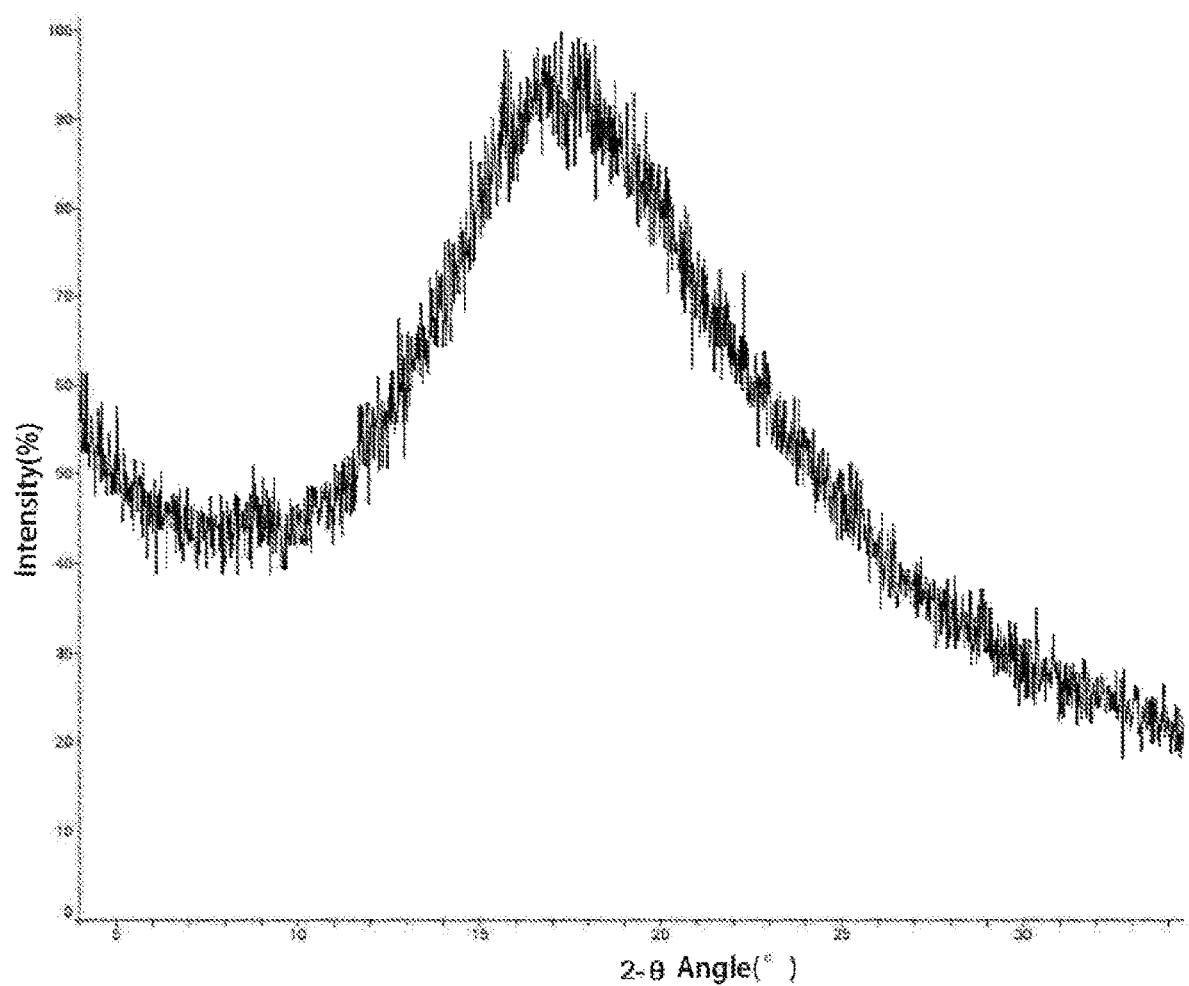
FIG. 1 is a Cu-Kα radiated XRPD spectrogram of the amorphous form of the compound of formula (I).

Hereinafter the present invention is described in details by ways of examples, but it is not intended to limit the present invention in any adverse manner. The present invention has been described in details herein, and further disclosed specific embodiments. It will be apparent to those skilled in the art that a variety of modifications and improvements can be made to the embodiments of the present invention without departing from the principle and scope of the present invention.

EXAMPLE 1

Preparation of the Compound of Formula (I)

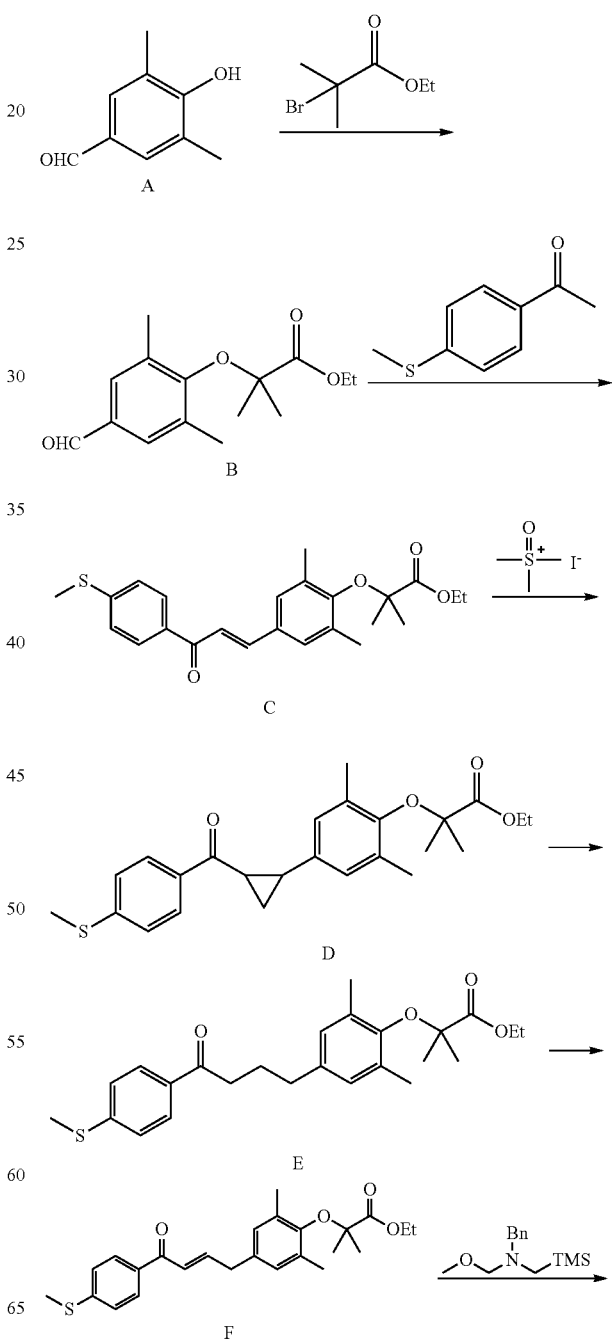

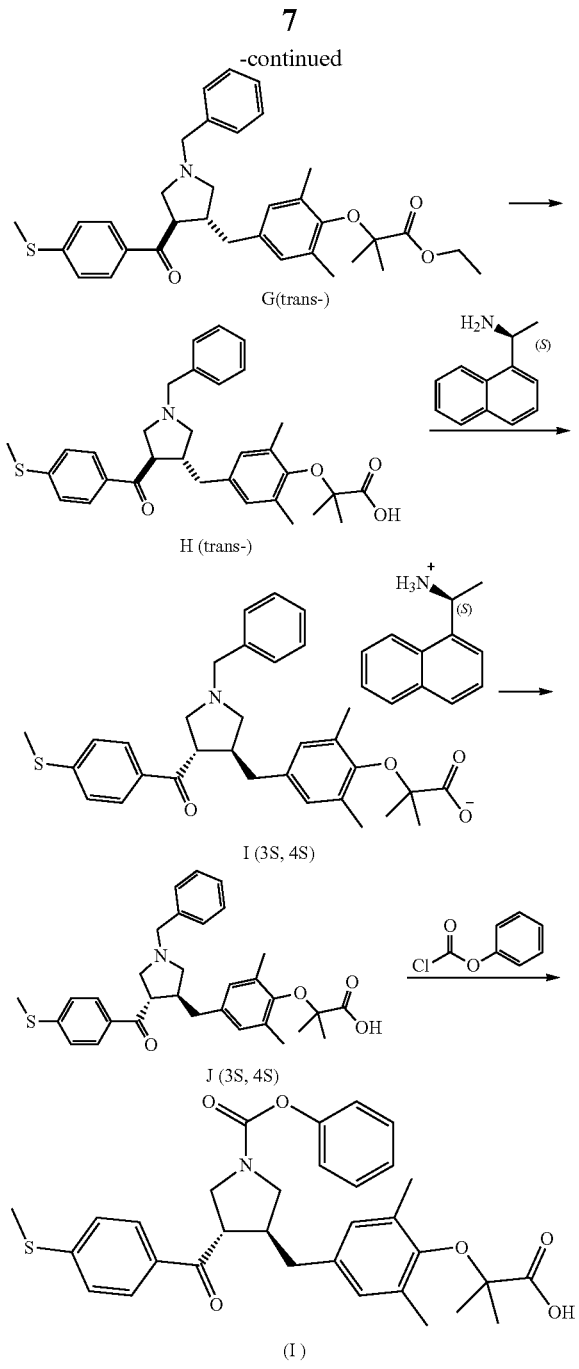

Step 1: Preparation of Compound B

At 25° C., acetonitrile (30 L) was added into a 50 L reactor, start stirring, and then Compound A (2.00 kg, 13.32 mol, 1.0 eq), ethyl bromoisobutyrate (7.79 kg, 39.95 mol, 3.0 eq) and potassium carbonate (5.52 kg, 39.95 mol, 3.0 eq) were added. The reaction solution was stirred at 80° C. for 16 h. The reaction temperature was cooled to 25° C., and then filtered. The filtrate was concentrated under reduced pressure. The resultant residue was dissolved in ethyl acetate (5 L). The filter cake was washed with ethyl acetate (5 L×2), and the ethyl acetate solutions were combined. The combined organic phases were washed with aq. NaOH (1 mol/L, 5 L/time) until showed that no spot of raw material A appeared in the organic phase by TLC (petroleum ether: ethyl acetate=5:1). The organic phase was washed with aqueous saturated solution of sodium chloride (5 L×2), dried over anhydrous sodium sulfate, filtered, and concentrated under reduced pressure, to give 1.51 kg of compound B, yield: 42.9%.

$^1$H NMR (400 MHz, CHLOROFORM-d) δ ppm 9.85 (s, 1H), 7.50 (s, 2H), 4.31-4.23 (m, 2H), 2.25 (s, 6H), 1.45 (s, 6H), 1.33 (t, J=7.2 Hz, 1H).

Step 2: Preparation of Compound C

In a dry ice-ethanol bath (−60° C.), gaseous HCl (3.67 kg, 100.54 mol, 5.3 eq) was introduced into ethanol (12 L), and the system temperature was controlled below 0° C. Ethanol (13 L) and the freshly prepared ethanol solution of HCl were added to a 50 L reactor. The mixture was stirred, and naturally warmed to 25° C. Then, compound B (5.01 kg, 18.97 mol, 1.0 eq) was added. After complete dissolution of the materials, p-methylthioacetophenone (2.83 kg, 17.07 mol, 0.9 eq) was added in portions. The mixture was stirred at 25° C. for 16 h. The reaction system was suction-filtered. The filter cake was dissolved in ethyl acetate (30 L), washed with water (10 L×2), aq. NaOH (1 N, 8 L×2), and aqueous saturated solution of sodium chloride (8 L×2), dried over anhydrous sodium sulfate (1.5 kg), filtered, and concentrated under reduced pressure to give 6.10 kg of compound C, yield: 76.8%.

MS m/z (ESI): 413.1 [M+1].

$^1$H NMR (400 MHz, CHLOROFORM-d) δ ppm 7.95 (d, J=8.28 Hz, 2H), 7.71 (d, J=15.56 Hz, 1H), 7.42 (d, J=15.56 Hz, 1H), 7.31-7.28 (m, 4H), 4.30 (q, J=7.28 Hz, 2H), 2.54 (s, 3H), 2.25 (s, 6H), 1.50 (s, 6H), 1.36 (t, J=7.15 Hz, 3H).

Step 3: Preparation of Compound D

N,N-dimethylformamide (15 L) was added to a 50 L reactor, start stirring, and trimethylsulfoxonium iodide (3.78 kg, 16.01 mol 1.2 eq) was added, then cooled to 0° C., and potassium tert-butoxide (1.79 kg, 16.01 mol, 1.2 eq) was added in portions. After the mixture was stirred at 0° C. for 30 min, a solution of compound C (5.5 kg, 13.34 mol, 1.0 eq) in N,N-dimethylformamide (15 L) was slowly added. The mixture was stirred at 0° C. for 2 h. The reaction liquor was slowly poured into ice water (0-5° C., 30 L), and then extracted with petroleum ether/ethyl acetate (1:1, 10 L×3). The combined organic phase was washed with water (10 L×2) and aqueous saturated solution of sodium chloride (10 L×2), dried over anhydrous sodium sulfate (2 kg), filtered, and concentrated under reduced pressure to give 5.48 kg of compound D, yield: 96.3%.

MS m/z (ESI): 427.2 [M+1].

$^1$H NMR (400 MHz, CHLOROFORM-d) δ ppm 7.91 (d, J=8.5 Hz, 2H), 7.27 (d, J=8.5 Hz, 2H), 6.81-6.70 (m, 1H), 6.75 (s, 1H), 4.29 (q, J=7.0 Hz, 2H), 2.83-2.74 (m, 1H), 2.56 (m, 1H), 2.51 (s, 3H), 2.18 (s, 6H), 1.84 (m, 1H), 1.46 (s, 6H), 1.35 (t, J=7.2 Hz, 3H).

Step 4: Preparation of Compound E

Ethanol (35.0 L) was added to a dry 50 L reactor, start stirring, and then compound D (5.45 kg, 12.79 mol, 1.0 eq) and glacial acetic acid (2.30 kg, 38.37 mol, 3.0 eq) were added. After heating the reaction mixture to 80° C., zinc powder (2.45 kg, 38.37 mol, 3.0 eq) was added in portions. The resultant suspension was continuously stirred at 80° C. for 16 h. The reaction liquor was filtered, and the filter cake was washed with ethyl acetate (3 L×2). The combined organic phase was concentrated under reduced pressure. The concentrated solution was dissolved in ethyl acetate (10 L), pump into a 50 L separatory funnel. Ethyl acetate (15 L) and water (10 L) were pumped into the 50 L separatory funnel and stirred for 5 minutes., then stood for phase separation. The organic phase was washed sequentially with 10% of aq. sodium carbonate (10 L×2) and aqueous saturated solution of sodium chloride (10 L×1), dried over anhydrous sodium sulfate, filtered, and concentrated under reduced pressure to give 5.15 kg of compound E, yield: 92.9%.

MS m/z (ESI): 429.2 [M+1].

$^1$H NMR (400 MHz, CHLOROFORM-d) δ ppm 7.74 (d, J=8.5 Hz, 2H), 7.17 (d, J=8.5 Hz, 2H), 6.71 (s, 2H), 4.21 (q, J=7.1 Hz, 2H), 2.82 (t, J=7.3 Hz, 2H), 2.51 (t, J=7.7 Hz, 2H), 2.45 (s, 3H), 2.09 (s, 6H), 1.94 (quin, J=7.5 Hz, 2H), 1.39 (s, 6H), 1.28 (t, J=7.0 Hz, 3H)

Step 5: Preparation of Compound F

Anhydrous dichloromethane (20 L) was added to a 50 L reactor, start stirring, then compound E (5.21 kg, 12.02 mol, 1.0 eq) and 2,6-lutidine (4.50 kg, 42.07 mol, 3.5 eq) were added. The mixture was cooled to 0° C. Trimethylsilyl trifluoromethanesulfonate (8.01 kg, 36.06 mol, 3.0 eq) was added to the reaction solution, and the mixture was continuously stirred at 0° C. for around 30 min. The reaction liquor was detected by TLC (petroleum ether:ethyl acetate=5:1). Cold water (5-10° C., 10 L) was pumped into a 50 L separatory funnel, and then pump into the reaction liquor under stirring. After stirring for 5 min, the phases were separated. The organic phase was washed with aqueous saturated solution of sodium chloride (10 L), and concentrated under reduced pressure. The concentrated solution was added to a mixed solution of methanol/water (2:1, 30 L) and stirred for about 20 min. Yellow solids were precipitated. The mixture was filtered, dried under reduced pressure to give a crude product as yellow solid.

Anhydrous toluene (35 L) was added to a 50 L reactor, start stirring, and the crude product which was dried under reduced pressure was added into the reactor. The mixture was cooled to 0° C., and Dichloro-dicyano-benzoquinone (2.99 kg, 13.22 mol, 1.1 eq) was added to the reactor in portions. The mixture was continuously stirred at 0° C. for 1h. The reaction liquor was detected by TLC (petroleum ether:ethyl acetate=5:1). Water (50 L) and sodium sulfite (3.00 kg) were added to a 120 L barrel. After being stirred to clear, the reaction liquor was slowly poured into the sodium sulfite solution, and ethyl acetate (15 L) was added. The mixture was quickly stirred for 10 min to precipitate a large amount of yellow solid, and then filtered by suction. The filter cake was washed with petroleum ether/ethyl acetate (3:1, 10 L×2). The filtrates were combined, and then the organic phase was separated. The organic phase was washed with 5% sodium sulfite (10 L×2) and aqueous saturated solution of sodium chloride (10 L×2), dried over anhydrous sodium sulfate (2.00 kg), filtered, and concentrated under reduced pressure (40-50° C.) to give 4.29 kg of crude product. Then, the crude product was added to 12 L of anhydrous ethanol, stirring at 25° C. for 0.5 h, then filtered. The filter cake was collected, and dried under reduced pressure to give 3.50 kg of compound F, yield: 69.9%.

MS m/z (ESI): 427.2 [M+1].

$^1$H NMR (400 MHz, CHLOROFORM-d) δ ppm 7.85 (d, J=8.5 Hz, 2H), 7.28-7.27 (m, 2H), 7.22-7.14 (m, 1H), 7.02 (s, 1H), 6.83 (s, 2H), 4.30 (s, 2H), 3.53 (d, J=6.8 Hz, 2H), 2.55 (s, 3H), 2.21 (s, 6H), 1.49 (s, 6H), 1.38 (s, 3H).

Step 6: Preparation of Compound G

2-Methyltetrahydrofuran (30 L) was added to a dry 50 L reactor, start stirring, and compound F (3.0 kg, 6.50 mol, 1.0 eq) and trifluoroacetic acid (37.05 g, 0.33 mol, 0.05 eq) were added. Then, N-(methoxymethyl)-N-(trimethylsilylmethyl) benzylamine (1.85 kg, 7.80 mol, 1.2 eq) was added slowly. The internal temperature was controlled below 30° C. After the dropwise addition, the mixture was continuously stirred at 25° C. for 12 h. The reaction liquor was bump into a 50 L separatory funnel, washed sequentially with 5% of aq. sodium carbonate (10 L×2) and aqueous saturated solution of sodium chloride(10 L×2), dried over anhydrous sodium sulfate (2 kg), filtered, and concentrated under reduced pressure to give 3.92 kg of compound G.

MS m/z (ESI): 560.0 [M+1].

$^1$H NMR (400 MHz, CHLOROFORM-d) δ ppm 7.71 (d, J=8.5 Hz, 1H), 7.31-7.20 (m, 9H), 6.71 (s, 1H), 4.30-4.23 (m, 2H), 3.76-3.36 (m, 6H), 3.07-2.96 (m, 2H), 2.68 (t, J=7.3 Hz, 2H), 2.51 (s, 3H), 2.10-2.03 (m, 6H), 1.36-1.22 (m, 9H).

Step 7: Preparation of Compound H

Compound G (3.92 kg, 5.04 mol, 1.0 eq) was dissolved in anhydrous ethanol (20 L), and the solution was added into a 50 L reactor, start stirring. NaOH (604.8 g, 15.12 mol, 3.0 eq) was dissolved in water (6 L), and then the solution was slowly added to the reaction solution. After addition, the mixture was continuously stirred at 25° C. for 16 h. The reaction solution was concentrated under reduced pressure to remove most of the solvent (ethanol). The concentrated solution was bumped into a 50 L separatory funnel, stirred, and then ethyl acetate (20 L) was added. The mixture was washed with 10% of aq. KHSO$_4$ (10 L×2) and aqueous saturated solution of sodium chloride(10 L×2), dried over anhydrous sodium sulfate (1.5 kg), and concentrated under reduced pressure until about 8 L of solvent was remained and a large amount of solid was precipitated. The concentration was stopped, and the mixture was cooled to 25° C. The concentrated suspension was filtered, and the filter cake was washed with ethyl acetate (2 L×3), dried by suction, and dried under reduced pressure in a vacuum drying chamber to give 2.44 kg of compound H, yield: 89.85%.

MS m/z (ESI): 532.1[M+1].

$^1$H NMR (400 MHz, CHLOROFORM-d) δ ppm 7.66 (dd, J=4.0, 8.3 Hz, 2H), 7.41-7.33 (m, 2H), 7.23-7.08 (m, 5H), 6.79 (d, J=2.0 Hz, 2H), 4.12 (q, J=7.0 Hz, 2H), 3.93-3.60 (m, 4H), 3.48-3.32 (m, 1H), 2.97-2.84 (m, 1H), 2.67 (d, J=7.8 Hz, 2H), 2.57-2.49 (m, 3H), 2.25-2.13 (m, 6H), 1.46 (s, 6H), 1.36 (t, J=7.2 Hz, 3H).

Step 8: Preparation of Compound I

Acetonitrile (24 L) and isopropanol (6 L) were added to a dry 50 L reactor, start stirring, then compound H (3.04 kg, 5.65 mol, 1.0 eq) was added. At 80° C., (S)-(-)-(1-naphthyl) ethamine (724.79 g) was slowly added. After addition, the mixture was continuously stirred at 80° C. for 1 h. The heating was stopped. The mixture was naturally cooled, and continuously stirred at 30° C. for 16 h. The stirring was stopped. The mixture was filtered by suction, and the filter cake was washed with isopropanol (2 L×2). After suction to dry, the solid was transferred into a rotatory evaporator to dry under reduced pressure to give 1.63 kg of compound I.

Chiral resolution conditions: Chiral column: Chiralpak AD-3 100×4.6 mm I.D., 3 μm; mobile phase: 40% methanol (0.05% DEA)-CO$_2$; flow rate: 4 mL/min; column temperature: 40° C.

The retention time of compound I: 1.604 min.

Step 9: Preparation of Compound J

Anhydrous ethanol (30 L) and anhydrous methanol (4.5 L) were added to a dry 50 L reactor, start stirring, and compound I (2.93 kg, 4.17 mol, 1.0 eq) was added. The mixture was heated to 80° C. and stirred for 1 h. The heating was stopped, and the mixture was naturally cooled. The mixture was continuously stirred at 30° C. for 16 h. The suspension was filtered by suction, and the filter cake was washed with ethanol (2 L×2), and dried under reduced pressure. methanol (1.5 L) and ethyl acetate (15 L) were added to the residue, and the mixture was stirred and then pump into a 50 L liquid separator. The organic phase was washed with 10% of aq. KHSO$_4$ (10 L×5), aqueous saturated solution of sodium chloride (5 L×2), dried over anhydrous sodium sulfate (1 kg), filtered, and concentrated under reduced pressure to give 0.97 kg of compound J.

Chiral resolution conditions: Chiral column: Chiralpak AD-3 100×4.6 mm I.D., 3 μm; mobile phase: 40% methanol (0.05% DEA)-$CO_2$; flow rate: 4 mL/min; column temperature: 40° C.

The retention of compound J: 1.576 min.

Step 10: Preparation of the Compound of Formula (I)

Anhydrous dichloromethane (7 L) was added to a dry 50 L reactor, start stirring, and compound J (700 g, 1.31 mol, 1.0 eq) and triethylamine (1.33 kg, 13.1 mol, 10.0 eq) were added. At 0° C., phenyl chloroformate (2.24 kg, 13.1 mol, 10.0 eq) was added dropwise to the reaction liquor. After completion of addition, the mixture was continuously stirred at 0° C. for 1 h. A solution of potassium carbonate (543.37 g, 3.94 mol, 3.0 eq) in pure water (3 L) was added to the reaction solution. The mixture was heated to 40° C. and continuously stirred for 20 min. Then, LiOH (165.60 g, 3.94 mol, 3.0 eq) was added, and the mixture was continuously stirred at 25° C. for 20 min. The reaction mixture was subjected to phase separation. The organic phase was washed with aqueous saturated solution of sodium chloride (2 L), dried over anhydrous sodium sulfate (500 g), filtered, and concentrated under reduced pressure. The concentrated solution was dissolved in ethyl acetate (1.5 L), then heptane (5.6 L) was slowly added under high-speed stirring. After addition, the mixture was continuously stirred for 30 min, and filtered. The filter cake was added to heptane/ethyl acetate (4:1, 3.5 L×3), and stirred at a high speed to beat for 30 min, and filtered. The resultant filter cake was dissolved in t-butyl methyl ether (5 L), and washed sequentially with 5% of aq. $KHSO_4$ (1.5 L×2), deionized water (1 L×2), dried over anhydrous sodium sulfate (300 g), filtered, and concentrated under reduced pressure. The resultant solid was dried in a vacuum oven (40-45° C.) to give the compound of formula (I).

MS m/z (ESI): 584.1 [M+23].

$^1$H NMR (400 MHz, MeOD-$d_4$) □δ ppm 7.65 (d, J=6.8 Hz, 2H), 7.43-7.37 (m, 2H), 7.29-7.22 (m, 3H), 7.16 (t, J=7.2 Hz, 2H), 6.87 (s, 2H), 4.13-3.92 (m, 2H), 3.89-3.80 (m, 1H), 3.69 (dd, J=5.4, 10.7 Hz, 1H), 3.58-3.49 (m, 1H), 2.81 (d, J=14.1 Hz, 2H), 2.71-2.63 (m, 1H), 2.55 (s, 3H), 2.23 (s, 6H), 1.43 (s, 6H).

Chiral resolution conditions: Chiral column: Chiralpak AD-3 100×4.6 mm I.D., 3 μm; mobile phase: 40% of methanol (0.05% DEA) in $CO_2$; flow rate: 2.8 mL/min; column temperature: 40° C.

The retention time of the compound of formula (I): 2.018 min.

EXAMPLE 2

Preparation of Amorphous Form of the Compound of Formula (I)

The temperature was controlled at 25° C., and the crude compound of formula (I) (310.5 g) as pale yellow solid was added to a 3 L reaction flask. Then, heptane (1500 mL) was added. After completion of addition, the reaction was stirred at 25° C. for 2 h, then filtered. The filter cake was washed with n-heptane (500 mL), then filtered to give a crude product. The crude product was dried in a vacuum drying chamber, and subjected to XRPD detection for its form. The obtained final product was in an amorphous form.

Figure 2:
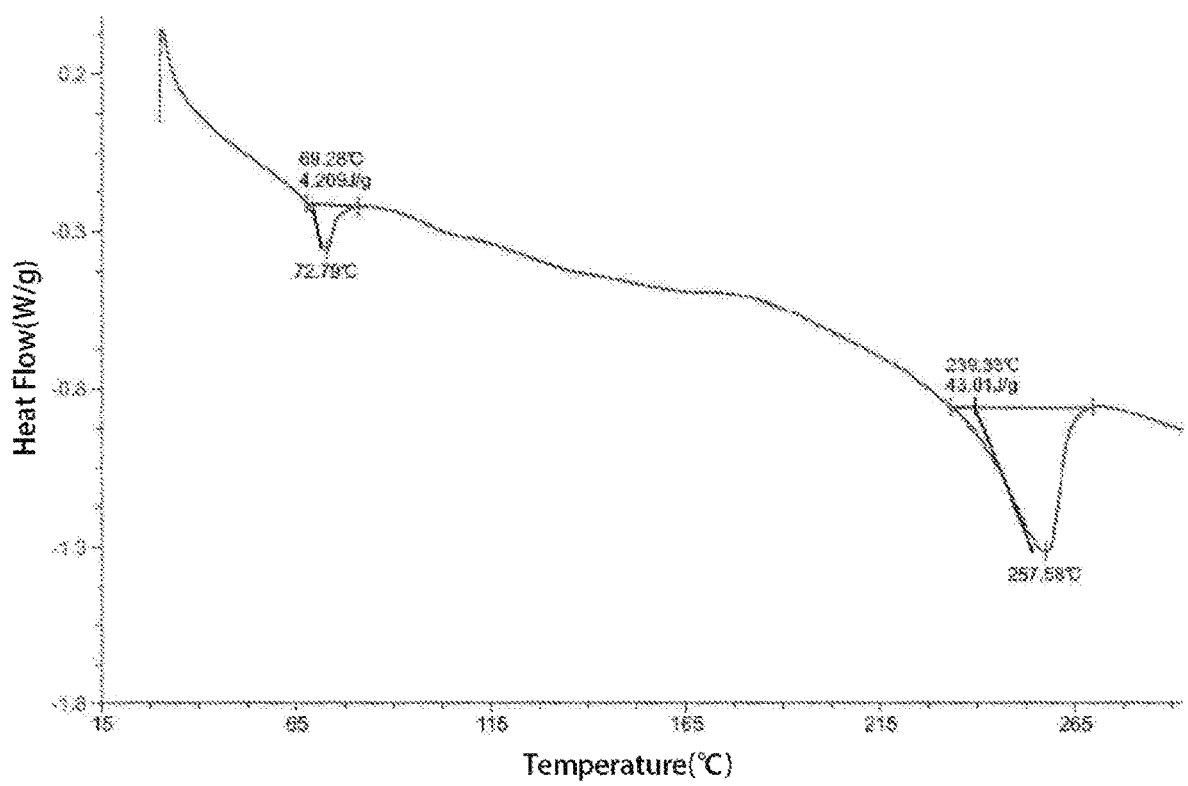
FIG. 2 is a DSC spectrogram of the amorphous form of the compound of formula (I).
Figure 3:
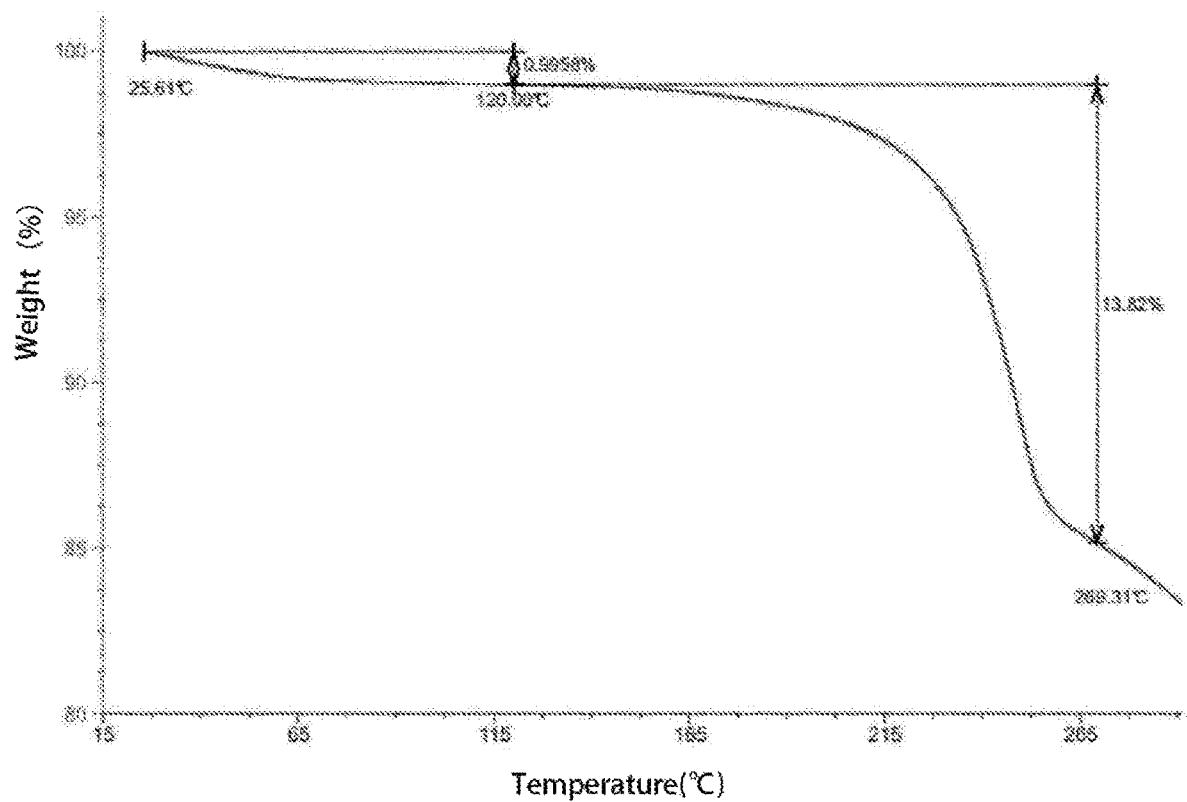
FIG. 3 is a TGA spectrogram of the amorphous form of the compound of formula (I).

The Cu-Kα radiated XRPD pattern of the obtained final product is shown in FIG. 1; the DSC pattern is shown in FIG. 2; and the TGA pattern is shown in FIG. 3.

EXAMPLE 3

Preparation of Amorphous Form of the Compound of Formula (I)

The compound of formula (I) (40.0 mg) was weighed and added to a 4.0 mL glass vial, and 150 μL of ethyl acetate was added to form a suspension. The suspension was stirred on a magnetic stirrer at 40° C. for 2 days, then the sample was centrifuged. The supernate was placed in a fuming cupboard until the solvent was dried off. Then, the resultant solid was dried in a vacuum drying chamber at 40° C. overnight. The resultant final product was amorphous form which was the same as that of Example 1.

EXAMPLE 4

Preparation of Amorphous Form of the Compound of Formula (I)

The compound of formula (I) (39.9 mg) was weighed and added to a 4.0 mL glass vial, and 150 μL of tetrafuran was added to form a suspension. After the suspension was stirred at 40° C. on a magnetic stirrer for 2 days, the sample was centrifuged, and the supernate was placed in a fuming cupboard until the solvent was dried off. Then, the obtained solid was dried in a vacuum drying chamber at 40° C. overnight. The resultant final product was amorphous form which was the same as that of Example 1.

EXAMPLE 5

Solid Stability Test of Amorphous Form of the Compound of Formula (I) Under High Temperature and High Humidity Conditions Samples (each about 100 mg) of the amorphous form of the compound of formula (I) were weighed in duplicates, and placed on the bottom of a glass sample bottle to spread out into a thin layer. The mouth of the glass sample bottle was sealed with aluminum foil which was pierced to form some holes thereon to ensure that the samples could sufficiently contact with the ambient air. The samples were placed in a constant temperature and humidity chamber at 40° C./75% humidity. The samples stored under the above conditions were sampled and tested on Days 10, 30, 60, and 90. The test results were compared with the initial test results of Day 0. The HPLC analysis method is shown in Table 1. The test results are shown in Table 2 below:

TABLE 1

| HPLC Analysis Method | |
| --- | --- |
| Column: | Waters Xbridge C18 (3.5 μm, 150 mm*4.6 mm) |
| Flow Rate: | 1.0 mL/min |
| Detection Wavelength: | 220 nm |
| Column Temperature: | 35° C. |
| Injection Volume: | 10 μL |
| Runtime: | 50 min |
| Mobile Phase: | Mobile phase A: 0.1% TFA-water |
| | Mobile phase B: acetonitrile |

TABLE 1-continued

HPLC Analysis Method

| | Time (min) | Mobile phase A (%) | Mobile phase B (%) |
|---|---|---|---|
| Gradient: | 0.00 | 90 | 10 |
| | 5.00 | 65 | 35 |
| | 35.00 | 5 | 95 |
| | 38.00 | 5 | 95 |
| | 40.00 | 90 | 10 |
| | 45.00 | 90 | 10 |
| Diluent | Water:acetonitrile = 50:50 (v/v) | | |
| ProbeWash | Water:acetonitrile = 50:50 (v/v) | | |

TABLE 2

Solid Stability Test of Amorphous form of the Compound of Formula (I)

| Time Point (Day) | Appearance | Purity (%) | Total Impurity (%) |
|---|---|---|---|
| 0 | Off-white powder | 97.37 | 2.63 |
| 10 | Off-white powder | 97.49 | 2.51 |
| 30 | Off-white powder | 97.31 | 2.69 |
| 60 | Off-white powder | 97.59 | 2.41 |
| 90 | Off-white powder | 97.28 | 2.72 |

The above experimental data shows that the amorphous form of the compound of formula (I) provided in the present invention does not exhibit a significant change in content and impurities at high temperature and humidity, and has relatively high stability at high temperature and humidity.

EXAMPLE 6

Solid Physical Stability Test of Amorphous Form of the Compound of Formula (I) at High Humidity Samples (each about 100 mg) of the amorphous form of the compound of formula (I) were weighed in duplicates, and placed on the bottom of a glass sample bottle to spread out into a thin layer. The mouth of the glass sample bottle was sealed with aluminum foil which was pierced to form some holes thereon to ensure that the samples could sufficiently contact with the ambient air. The prepared samples were placed under the relative conditions of 25° C./92.5%, and detected for their physical stability on Day 10. Meanwhile, a sample (about 100 mg) of the amorphous form of the compound of formula (I) was separately weighed, placed on the bottom of the glass sample bottle which was sealed with a screw cap, and stored at −20° C. as control. On Day 10, all the samples were taken out and returned to room temperature. The samples were visually observed for their appearance changes, and detected by XRPD for their forms. By comparing the accelerated sample with the control sample, the solid physical stability of the compound of formula (I) was determined. Table 3 as below shows results of the solid physical stability experiments of the amorphous form of the compound of formula (I).

TABLE 3

Solid Physical Stability Tests of the Amorphous Form of the Compound of Formula (I) at High Humidity

| Item | Time Point | 25° C./92.5% Relative Humidity (Open) |
|---|---|---|
| Form | Day 10 | Amorphous |
| Appearance | Day 10 | Off-white powder |

The above experimental data shows that the amorphous form of the compound of formula (I) provided in the present invention does not exhibit form and appearance changes at high humidity, and has relatively high stability at high humidity.

EXAMPLE 7

Stability Tests of the Amorphous Form of the Compound of Formula (I) in Various Solvents A plurality of samples of the amorphous form of the compound of formula (I) (each about 20 mg) were respectively added to 0.3-0.4 mL of a single or mixed solvent as listed in the table below, and stirred at 40° C. After being stirred for 2 days, if the sample was still in a state of a solution or close to a solution, it was filtered, followed by natural evaporation of solvent; and if the sample was still a suspension, the sample was centrifuged for collecting the precipitates, and the supernate was placed in a fuming cupboard until the solvent was dried off. Then, the precipitates and the solids obtained after solvent evaporation were placed in a vacuum drying oven at 40° C. overnight. The solids in all the samples were collected and detected by XRPD for their states. The results are shown in Table 4.

TABLE 4

Stability tests of the amorphous form of the compound of formula (I) in various solvents

| No. | Solvent | Appearance | Results |
|---|---|---|---|
| 1 | Methanol | Solid precipitated after evaporation of solvent | Amorphous |
| 2 | Ethanol | Suspension (2 days)/Solid precipitated after evaporation of solvent. | Both amorphous |
| 3 | Acetonitrile | Suspension (2 days)/Solid precipitated after evaporation of solvent. | Both amorphous |
| 4 | Acetone | Suspension (2 days)/Solid precipitated after evaporation of solvent. | Both amorphous |
| 5 | Ethyl acetate | Suspension (2 days)/Solid precipitated after evaporation of solvent. | Both amorphous |
| 6 | Tetrafuran | Suspension (2 days)/Solid precipitated after evaporation of solvent. | Both amorphous |
| 7 | 1,4-dioxane | Suspension (2 days)/Solid precipitated after evaporation of solvent. | Both amorphous |
| 8 | Methanol:water = 3:1 | Solid precipitated after evaporation of solvent. | Amorphous |
| 9 | Ethanol:water = 3:1 | Suspension (2 days)/Solid precipitated after evaporation of solvent. | Both amorphous |
| 10 | Acetonitrile:water = 3:1 | Suspension (2 days)/Solid precipitated after evaporation of solvent. | Both amorphous |
| 11 | Acetone:water = 3:1 | Suspension (2 days)/Solid precipitated after evaporation of solvent. | Both amorphous |

The above experimental data shows that the amorphous form of the compound of formula (I) provided in the present invention does not exhibit any change of form, and has relatively high stability.

Bioactivity Test

EXPERIMENTAL EXAMPLE 8

In Vitro Evaluation

Principles of in Vitro Test of PPAR Agonist Activity

Nuclear Hormone Receptor (NHR) Test

PathHunter's NHR protein interaction and nuclear transfer test are used to detect the activation ability of nuclear hormone receptor in a uniform, non-imaging experiment. This technology is called as enzyme fragment complementation (ETC), and is developed by DiscoverX.

NHR protein test is based on the detection of the protein-protein interaction between a standard length of NHR protein in an activated state and a nuclear fusion protein containing a steroid receptor co-activating peptide (SRCP) region and one or more standard LXXLL acting sequences. NHR is labeled on the ProLink™ component of an EFC test system, and the SRCP region and the enzyme receptor component (EA) are fused and expressed in the nucleus. When bound to the ligand, the NHR will transfer to the nucleus and obtain the SRCP region in which a complementary effect is produced, thereby generating an equivalent amount of activated-galactosidase (-Gal), accompanied by the generation of chemical light signals. The benefits associated with this pathway include reduced incubation time of the compound, direct test of an NHR target, use of human NHR sequences with a standard length, and selection of some new classes of compounds based on the disruption of protein-protein interactions.

The NHR NT test detected the transfer of an NHR between the cytoplasmic and nuclear compartments. The receptor was labeled on the ProLink™ component of the EFC test system, while the EA and nuclear sequence were fused, thereby limiting the expression of EA on the nucleus. Nucleus transfer leaded to the complementary effect with EA, thereby generating one equivalent of activated galactosidase (-Gal), accompanied by the generation of chemical light signals.

Cell Processing:

1. PathHunter NHR cell strains were spread from a frozen stock in accordance with standard operations.

2. Cells were seeded onto a 384-well white cell plate of 20 uL/well, and incubated at 37° C. for an appropriate time prior to test. The culture medium contained activated carbon dextran with filtered serum to reduce the level of hormone expression.

Experiments of Agonist Mode:

1. As for the measurement of an agonist activity, it is required to incubate the cells with the compound to induce a response.

2. The compound was formulated with a buffer solution to a stock solution, which was 5×diluted.

3. 5 uL of 5×diluted solution of the compound was added to the cells, and incubated at 37° C. (or room temperature) for 3-16 h, ensuring that the final concentration of the media was 1%).

Experiments of Inhibitor Mode:

1. As for the measurement of inhibitory activity, it is required to incubate the cells with the anti-agonist, and then challenged with an agonist at the EC80 concentration.

2. The compound was formulated with a buffer solution to a stock solution, which was 5×diluted.

3. 5 uL of 5×diluted solution of the compound was added to the cells, and incubated at 37° C. (or room temperature) for 60 min, ensuring that the final concentration of the media was 1%).

4. 5 uL of EC80 agonist which was 6×diluted with a buffer solution was added to the cells, and incubated at 37° C. (or room temperature) for 3-16 h.

Signal Detection:

1. The experimental signals were generated by 12.5 uL or 15 uL (50% v/v) of the PathHunter test reagent mixture which was once added, then needed to be incubated at room temperature for 1 h.

2. The chemiluminescence signals generated by the microplate were to be detected by a PerkinElmer Envision instrument.

Data Analysis:

1. The activity of the compound was analyzed by CIBS data analysis software (ChemInnovation, CA).

2. For experiments of agonist mode, the percentage activity is calculated by the following formula:

% activity=100%×(the mean RLU of the compound to be tested−the mean background RLU of the medium)/(the mean of maximum control of the ligand−the mean background RLU of the medium)

3. For experiments of antagonist mode, the percentage activity is calculated by the following formula:

% Inhibition=100%×(1−(the mean RLU of the compound to be tested−the mean background RLU of the medium)/(the mean RLU of the EC80 control compound−the mean background RLU of the medium))

4. It should be noted that the response of the ligand causes a decrease in the activity of the receptor (have inverse agonist with a continuous active target). The activity of these inverse agonist is calculated by the following formula:

% Inverse agonist activity=100%×((the mean background RLU of the medium−the mean RLU of the compound to be tested)/(the mean background RLU of the medium−the mean RLU of the maximum control of ligand))

The experimental results are shown in Table 5:

TABLE 5

In Vitro Screening Experimental Results of the Compound of the Present Invention

| Compound | PPAR Alpha | | PPAR Delta | | PPAR Gamma | |
|---|---|---|---|---|---|---|
| | $EC_{50}$ nM | Maximum stimulus-response value % | $EC_{50}$ nM | Maximum stimulus-response value % | $EC_{50}$ nM | Maximum stimulus-response value % |
| GW7647 | A | 100% | / | / | / | / |
| L-165,041 | / | / | A | 100% | / | / |
| Troglitazone | / | / | / | / | E | 100% |
| GFT-505 (Elafibranor) | E | I | C | II | E | II |
| Compound of formula (I) | A | I | A | II | E | I |

Note 1:
Based on 100% of the maximum stimulus-response value of in vitro platforms of the known PPAR α agonist GW7647, PPAR δ agonist L-165,041, and PPAR γ agonist Troglitazone, the maximum response values of other compounds are compared with the maximum stimulus-response value to give the corresponding maximum value of stimulus-response. It is generally considered that a compound with the maximum stimulus-response value greater than 80% is a full agonist, a compound with the maximum stimulus-response value greater than 50% and less than 80% is a partial agonist, and a compound with the maximum stimulus-response value less than 50% has an incomplete agonistic effect.

Note 2:
A $\leqslant$ 100 nM; 100 nM < B $\leqslant$ 150 nM; 150 nM < C $\leqslant$ 200 nM; 200 nM < D $\leqslant$ 250 nM; E > 250 nM.

Note 3:
100% $\geqslant$ I $\geqslant$ 80%; 80% > II $\geqslant$ 50%; III < 50%.

The above experimental data shows that the compound of formula (I) has a significant activation effect on PPAR Alpha and Delta receptors, and a selective activation effect on a PPAR Gamma receptor.

Based on the above evaluation experiments on the stability and activity of the amorphous form of the compound of formula (I), it can be seen that: unlike the conventional knowledge of amorphous drugs in the field, the amorphous form of the compound of formula (I) provided in the present invention form has a high stability in terms of chemical properties and physical forms. Also, the amorphous form of the compound of formula (I) produces an obvious inhibition effect on cytokines associated with PPAR-related pathways, and has significant effects in improving liver injury, NAS Score and liver fibrosis. It can be seen that the amorphous form of the compound of formula (I) has good medicinal prospects.

The invention claimed is:

1. An amorphous form of a compound represented by formula (I),

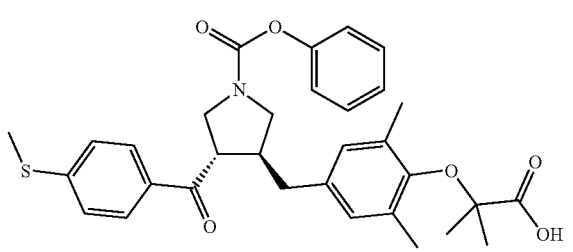

(I)

wherein an X-ray powder diffraction pattern of the amorphous form is shown in FIG. 1.

2. The amorphous form according to claim 1, wherein a differential scanning calorimetry curve of the amorphous form has starting points of two endothermic peaks at 69.28±3° C. and 239.33±3° C.

3. The amorphous form according to claim 2, wherein a DSC pattern of the amorphous form is shown in FIG. 2.

4. The amorphous form according to claim 1, wherein a thermogravimetric analysis curve of the amorphous form has a weight loss reached 0.9958% at 120.00±3° C.

5. The amorphous form according to claim 4, wherein a TGA pattern of the amorphous form is shown in FIG. 3.

* * * * *